US012748097B2

(12) United States Patent
Molla et al.

(10) Patent No.: US 12,748,097 B2
(45) Date of Patent: Sep. 29, 2026

(54) METHOD OF DETERMINING SATURATES, AROMATICS, RESINS, AND ASPHALTENE (SARA) FRACTIONS OF RESERVOIR FLUID DURING DOWNHOLE FLUID ANALYSIS

(71) Applicant: Schlumberger Technology Corporation, Sugar Land, TX (US)

(72) Inventors: Shahnawaz Hossain Molla, Acton, MA (US); Lalitha Venkataramanan, Lexington, MA (US); Trent Kristinn Walsh, Abu Dhabi (AE)

(73) Assignee: Schlumberger Technology Corporation, Sugar Land, TX (US)

( * ) Notice: Subject to any disclaimer, the term of this patent is extended or adjusted under 35 U.S.C. 154(b) by 183 days.

(21) Appl. No.: 18/745,709

(22) Filed: Jun. 17, 2024

(65) Prior Publication Data

US 2024/0418698 A1 Dec. 19, 2024

Related U.S. Application Data

(60) Provisional application No. 63/508,661, filed on Jun. 16, 2023.

(51) Int. Cl.

| | |
|---|---|
| ***G01N 21/00*** | (2006.01) |
| ***G01N 15/075*** | (2024.01) |
| ***G01N 21/31*** | (2006.01) |
| ***G01N 27/06*** | (2006.01) |
| ***G01N 33/28*** | (2006.01) |

(52) U.S. Cl.
CPC ....... *G01N 33/2835* (2013.01); *G01N 15/075* (2024.01); *G01N 21/31* (2013.01); *G01N 27/06* (2013.01); *G01N 33/2823* (2013.01); *G01N 2201/0635* (2013.01)

(58) Field of Classification Search
CPC ...... E21B 2200/22; E21B 47/06; E21B 49/08; E21B 49/0875; E21B 49/10
See application file for complete search history.

(56) References Cited

PUBLICATIONS

WO2020131996A1 (Year: 2020).*
Adyani, W.N. et al., "A Systematic Approach to Evaluate Asphaltene Precipitation During CO2 Injection" SPE-143903-MS, SPE Enhanced Oil Recovery Conference, Jul. 19, 2011, pp. 1-27.
Dahaghi, A.K. et al., "Formation Damage Through Asphaltene Precipitation Resulting From CO2 Gas Injection in Iranian Carbonate Reservoirs" SPE-99631-PA, SPE Production Operations, May 19, 2008, pp. 210-214, 23, 2.

(Continued)

*Primary Examiner* — Dani Fox
(74) *Attorney, Agent, or Firm* — Jeffrey D. Frantz

(57) ABSTRACT

Systems and methods for estimating the SARA fractions of a reservoir fluid. This method uses a machine learning (ML) based model to predict the SARA fractions of a reservoir fluid. The ML models are trained using conventional laboratory data, such as fluid composition from gas chromatography, SARA measurement, Asphaltene onset pressure (AOP), etc. Reservoir fluid can be pumped from a wellbore into a downhole fluid analyzer tool. The downhole fluid analyzer tool can take measurements indicating the presence and levels of certain particles in the fluid. The measurements can be applied to the ML models to estimate SARA levels in the reservoir fluid.

20 Claims, 4 Drawing Sheets

(56) References Cited

PUBLICATIONS

Dong, C. et al., "New Downhole-Fluid-Analysis Tool For Improved Reservoir Characterization" SPE-108566-PA, SPE Reservoir Evaluation Engineering, vol. 11, No. 06, Dec. 29, 2008, pp. 1-11.
Gonzalez, D.L. et al., "Effects of Gas Additions to Deepwater Gulf of Mexico Reservoir Oil: Experimental Investigation of Asphaltene Precipitation and Deposition" SPE-159098-MS, SPE Annual Technical Conference and Exhibition, Oct. 8, 2012, pp. 1-11.
Hammami, A. et al., "Asphaltene Precipitation From Live Oils: An Experimental Investigation of Onset Conditions and Reversibility" Energy Fuels, vol. 14, Issue 01, Dec. 15, 1999, pp. 14-18.
Jamaluddin, A.K.M. et al., "A Comparison of Various Laboratory Techniques to Measure Thermodynamic Asphaltene Instability" SPE-72154-MS, SPE Asia Pacific Improved Oil Recovery Conference, Oct. 8, 2001, pp. 1-17.
Jamaluddin, A.K.M. et al., "An Investigation of Asphaltene Instability Under Nitrogen Injection" SPE-74393-MS, SPE International Petroleum Conference and Exhibition, Feb. 10, 2002, pp. 1-10.
Joshi, N.B. et al., "Asphaltene Precipitation From Live Crude Oil" Energy Fuels, vol. 15, Issue 04, Apr. 23, 2001, pp. 979-986.

* cited by examiner

METHOD OF DETERMINING SATURATES, AROMATICS, RESINS, AND ASPHALTENE (SARA) FRACTIONS OF RESERVOIR FLUID DURING DOWNHOLE FLUID ANALYSIS

CROSS REFERENCE

This application claims the benefit of U.S. Provisional Patent App. No. 63/508,661, "Method of Determining Saturates, Aromatics, Resins, and Asphaltene (SARA) Fractions of Reservoir Fluid During Downhole Fluid Analysis," filed Jun. 16, 2023, the complete disclosure of which is hereby incorporated herein by reference.

BACKGROUND

Oil & Gas companies, find, assess, produce, and sell fluids. Starting from exploration to production, there is a need to measure and quantify the uncertainty associated with the value of their product, namely, reservoir fluids. Through these measurements, useful information is generated about the reservoir fluid in every step.

Asphaltenes are recognized as the most polar components in crude oil, characterized by their solubility properties; specifically, asphaltenes dissolve in toluene but remain insoluble in an excess of heptane. These substances can deposit in various parts of the oil production infrastructure, such as reservoirs, wellbore tubing, flow lines, and separators. Such deposits can obstruct and potentially halt production by forming plugs. During oil production, the solubility of asphaltenes in crude oil diminishes as the pressure drops while the fluid moves through the reservoir and wellbore. The asphaltene onset pressure ("AOP") is defined as the pressure at which asphaltenes start to precipitate at a constant temperature. Asphaltene deposition can commence deep within the wellbore while the pressure is still significantly higher than the bubble point. Additionally, asphaltenes may precipitate during miscible flooding with carbon dioxide ("CO2") and natural gases, as well as from the commingling of different fluids.

Identifying the conditions that trigger asphaltene precipitation in reservoir fluids is crucial for both upstream and downstream operations. Understanding asphaltene behavior is essential to optimize flow assurance and prevent undesirable asphaltene precipitation during oil production and processing.

It is imperative for operators to detect the presence of problematic asphaltenes in reservoir fluids at the earliest stage possible. Moreover, comprehending the conditions that cause asphaltene precipitation is vital. The concentration of asphaltenes and their tendency to precipitate or deposit can significantly impact the value of a reservoir. Asphaltenes also affect downstream operations, such as those in refineries. Therefore, early detection of asphaltene concentration and potential precipitation is critically important.

One widely used method for compositional analysis of petroleum samples is a SARA (saturates, aromatics, resins, and asphaltenes) fractionation test, also known as SARA analysis. SARA fractionation serves as a screening criterion for asphaltene stability in reservoir fluids due to pressure depletion or the mixing of different fluids. This fractionation is based on the solubility of hydrocarbon components in various solvents utilized in the test. Each fraction represents a solubility class containing a range of molecular-weight species. In this method, crude oil is divided into four solubility classes collectively known as SARA: saturates, aromatics, resins, and asphaltenes. Saturates typically consist of iso- and cyclo-paraffins, while aromatics, resins, and asphaltenes form a continuum of molecules with increasing molecular weight, aromaticity, and heteroatom content. Asphaltenes may also include metals such as nickel and vanadium.

A need exists for estimating SARA fractions in fluid of a reservoir.

SUMMARY

Examples described herein include systems and methods for estimating the SARA fractions of a reservoir fluid. This method uses a machine learning ("ML") based model to predict the SARA fractions of a reservoir fluid. The ML models are trained using conventional laboratory data, such as fluid composition from gas chromatography, SARA measurement, AOP, etc. Specific input features are incorporated in this model to accurately predict SARA fractions.

This method enables prediction of SARA fractions using downhole measurements. The trained models are designed to predict SARA fractions from downhole fluid composition and peripheral measurements as obtained from downhole sensors. Other methods are based on laboratory fluid analysis.

The system enables prediction of SARA fractions using downhole measurements. The trained models are designed to predict SARA fractions from downhole fluid composition and peripheral measurements as obtained from downhole sensors by using a Downhole Fluid Analyzer ("DFA") module.

Both the foregoing general description and the following detailed description are exemplary and explanatory only and are not restrictive of the examples, as claimed.

DESCRIPTION OF THE EXAMPLES

Reference will now be made in detail to the present examples, including examples illustrated in the accompanying drawings. Wherever possible, the same reference numbers will be used throughout the drawings to refer to the same or like parts.

Figure 2:
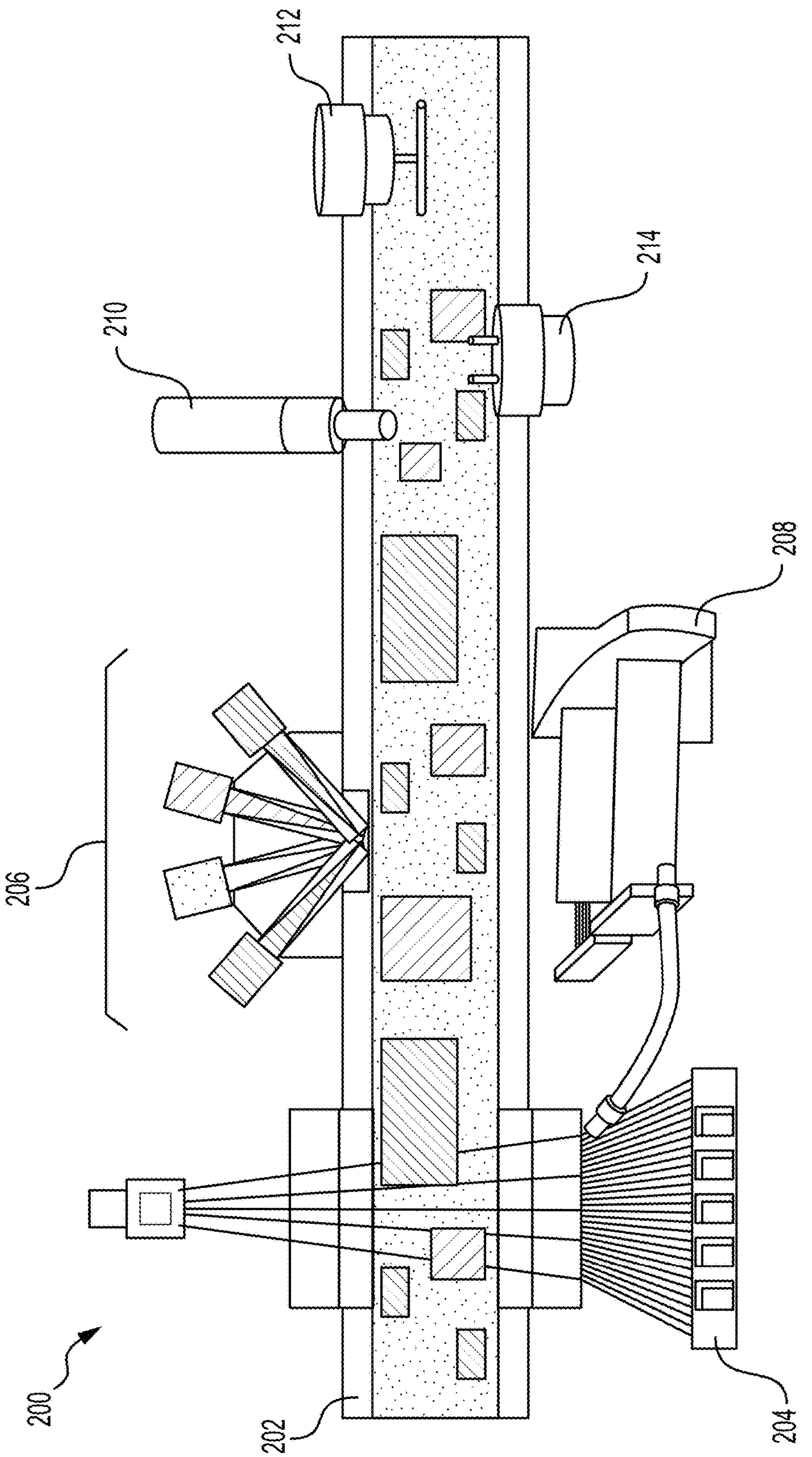
FIG. 2 is a schematic diagram illustrating an example arrangement of a DFA optical module and other sensors in a flowline.

Systems and methods are described herein for estimating the SARA fractions of a reservoir fluid. In subsurface condition, a DFA tool is used to measure basic fluid composition of the formation fluid at reservoir pressure and temperature and use these measurements to identify the fluid type and predict gas-oil-ratio of the fluid. These measurements play a crucial role in ensuring that the formation fluid sample collected downhole has minimum level of contamination. The composition is inferred by measuring the optical information of the formation fluid using a downhole spectrometer (FIG. 2). Additionally, the pressure, temperature, density and viscosity of the fluid is concurrently measured.

Figure 1:
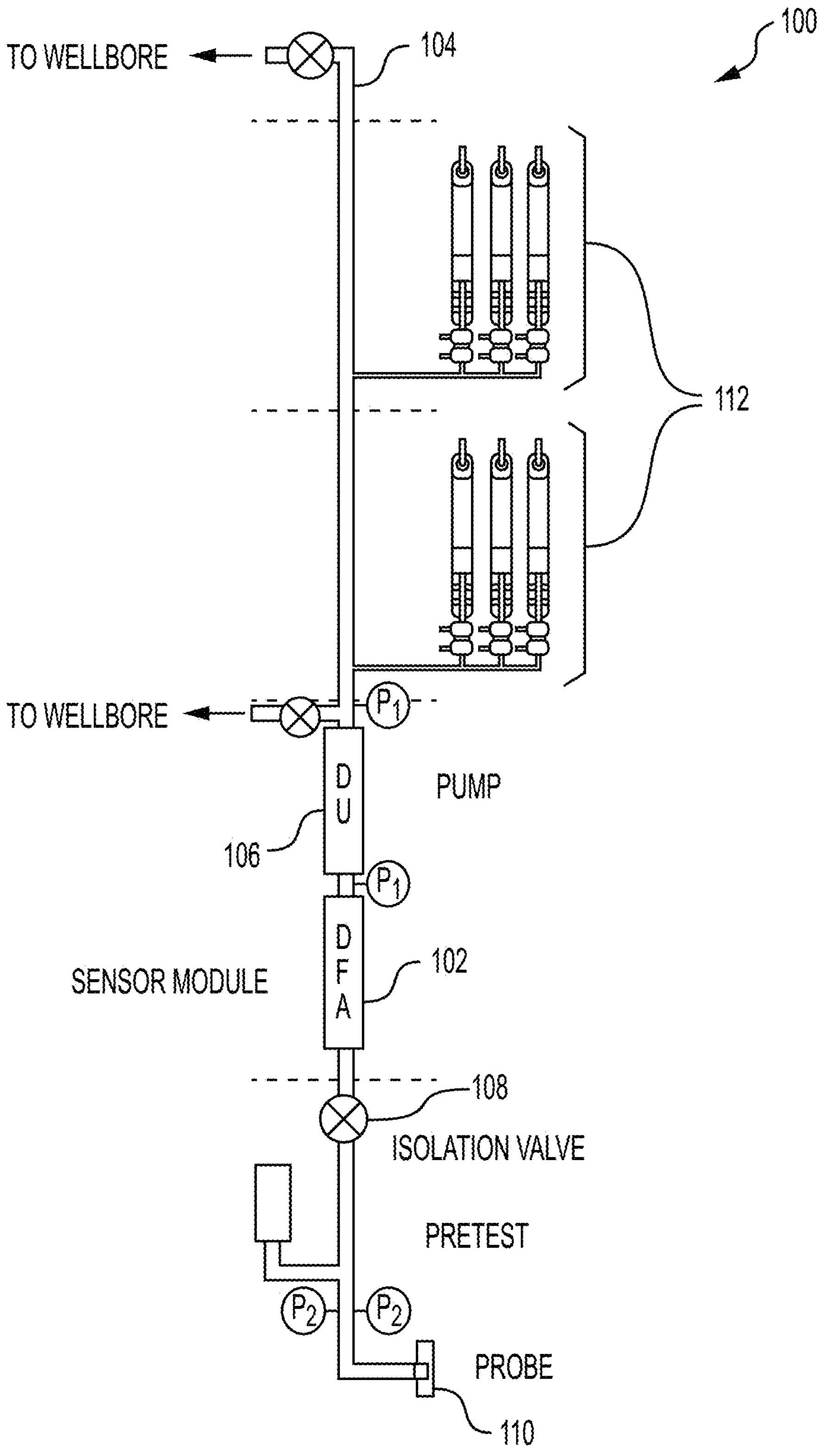
FIG. 1 is a schematic diagram illustrating an example tool string with downhole fluid analysis DFA module.

FIG. 1 shows a schematic of a DFA tool 100 with the DFA module 102. The DFA tool 100 can include a series of components that are lowered into a wellbore. The DFA tool 100 can includes tubes 104 or piping that are lowered into one or more wellbores. The DFA tool can include various structural components 112 that support the tubes 104 in facilitating fluid transfer to the DFA module 102. A pump 106 can pump fluid from the wellbores through the DFA module and into an isolation valve 108. The isolation valve 108 is a specialized valve used to control the flow of fluids within the wellbore. The isolation valve 108 functions as a gate that can be opened or closed to stop the flow of oil, gas, or water at a specific point. The DFA tool 100 can also include a probe 110. The probe 110 can include sensors that measure various formation properties, such as porosity, permeability, and the presence of oil and gas.

FIG. 2 is a schematic diagram illustrating an example arrangement of a DFA optical module 200 in a flowline. The DFA optical module 200 can collect optical information of the fluid in the flow line using a downhole filter array spectrometer 204. The spectrometer 204 measures optical absorbance of the fluid at multiple wavelengths. These optical spectra are processed to identify the fluid type (oil, gas, gas condensate) and to quantify the weight fraction of hydrocarbons (methane, ethane, propane, n-butane, n-pentane, and hexane plus) and carbon dioxide in the fluid.

The filter array spectrometer 204 can be a type of spectrometer that utilizes an array of filters to separate light into its constituent wavelengths, for measuring the spectral content of light. The filter array spectrometer 204 can include a light source, a filter array, and a detector array. The filter array can consist of a grid or pattern containing numerous narrowband filters, each designed to transmit a specific range of wavelengths. These filters can be arranged in various configurations, like a one-dimensional linear array or a two-dimensional matrix. The detector array can be placed directly behind the filter array. Non-exhaustive examples of a detector array include a Charge-Coupled Device ("CCD") or a Complementary Metal-Oxide-Semiconductor ("CMOS") sensor. The detector array can have multiple pixels, corresponding to the number of filters in the filter array.

The DFA optical module 200 can include a fluorescence detector 206. The fluorescence detector 206 can be used to analyze the type of fluids present in a reservoir. The fluorescence detector 206 measures the fluorescence emitted by the reservoir fluids, which can help to differentiate between oil, gas, and water. This information is valuable for reservoir characterization and optimizing production strategies.

The DFA optical module 200 can include a grating spectrometer 208. A beam of light can be directed into the spectrometer 208. The light encounters a diffraction grating, which is a panel containing thousands of tiny parallel grooves. As light passes through these grooves, it diffracts (bends) at specific angles depending on the wavelength of the light. Shorter wavelengths bend more than longer wavelengths. This diffraction separates the light beam into its constituent colors (wavelengths), similar to how a prism separates white light into a rainbow. The separated wavelengths of light fall onto a detector, which measures the intensity of light at each wavelength. By analyzing the intensity pattern at different wavelengths, the grating spectrometer 208 can identify the presence and abundance of specific chemicals in the sample. This is because different molecules absorb and emit light at characteristic wavelengths. This allows the DFA optical module 200 to identify and quantify the components of downhole fluids.

The DFA optical module 200 can include a pressure/temperature ("P/T") gauge 210. The P/T gauge 210 can measure the force exerted by a gas or liquid on a surface within the DFA optical module 200. The P/T gauge 210 can also measure the temperature of the gas or liquid.

The DFA optical module 200 can include density and viscosity sensor 212. The viscosity sensor 212 measures the resistance to flow of oil or other fluids encountered during drilling, production, or transportation. Viscosity is a crucial property of these fluids as it impacts various aspects of oil and gas operations.

The DFA optical module 200 can include a resistivity sensor 214. The resistivity sensor 214 can measure the ability of a formation or fluid to conduct an electrical current. This electrical conductivity is inversely proportional to resistivity—the higher the resistivity, the lower the ability to conduct electricity.

The various components of the DFA module 200 can be encased or coupled to a housing 202. In an example, the housing 202 can be a flowbore housing in which fluid can pass through.

Figure 3:
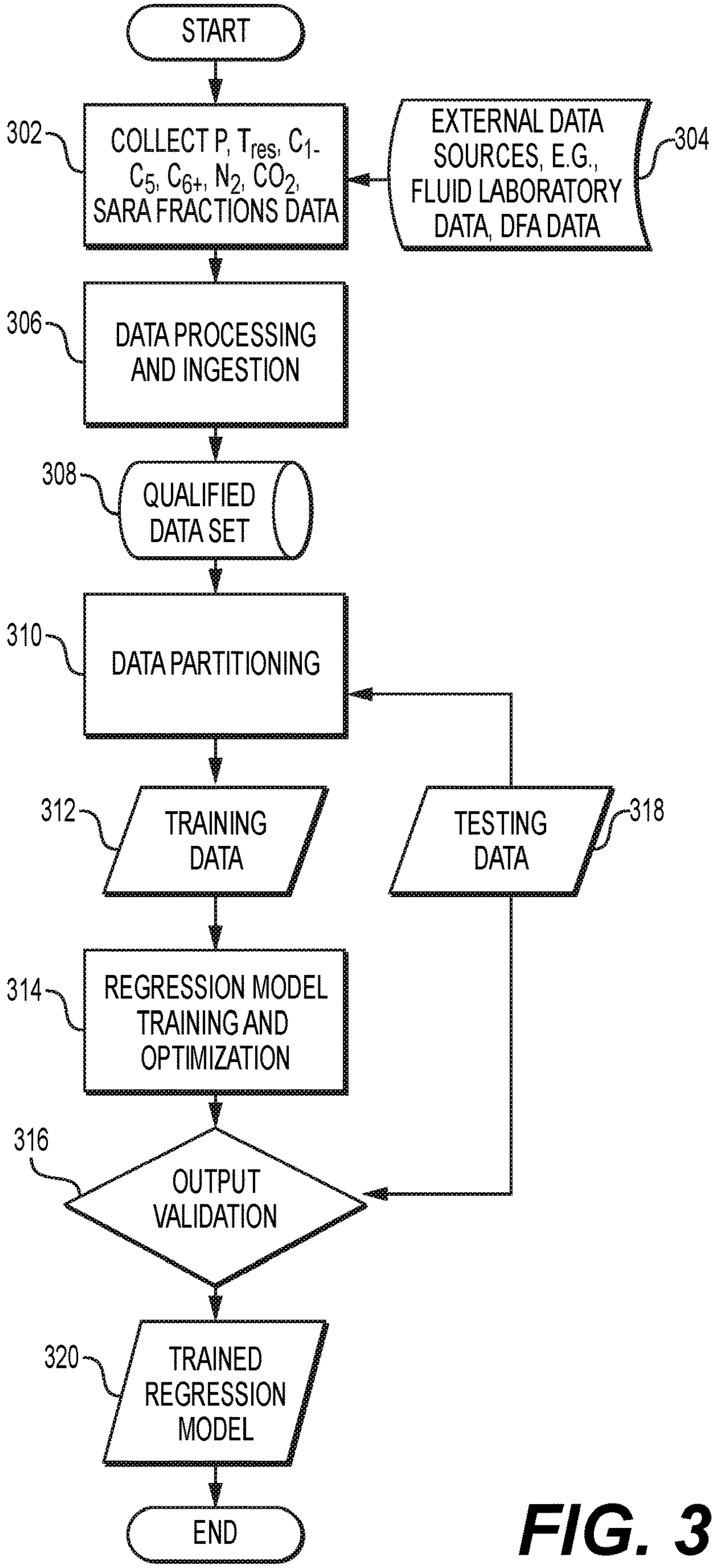
FIG. 3 is an illustration of an example workflow for estimating SARA fractions of a reservoir fluid based on data from downhole sensors.

FIG. 3 shows a workflow for training a model for estimating SARA fractions of a reservoir fluid based on data from downhole sensors. At stage 302, a computing device can collect sample data for downhole wells related to pressure ("P"), temperature ("Tres"), methane ("C1"), ethane ("C2"), propane ("C3"), butane ("C4"), pentane ("C5"), hexanes ("C6+"), nitrogen ("N2"), CO2, and SARA fractions data. The computing device can be one or more processor-based devices, such as a personal computer, tablet, mobile phone, or server. The computing device can collect the data from an external source, such as a fluid laboratory 304.

At stage 306, the computing device can ingest and process the data. For example, the computing device can gather the raw sample data and import it into a system for further processing. The computing device can then process the sample data to transform it into a usable format. This can include cleansing the data (e.g., removing inaccuracies, handling missing values, and correcting errors), transforming the data (e.g., normalizing, aggregating, and enriching the data), and integrating any other necessary data.

At stage 308, processing the data can result in a qualified data set. A qualified data set can be a collection of data that meets specific criteria ensuring it is suitable for its intended purpose. This involves various aspects of quality, relevance, and integrity. A qualified data set is essential for reliable data analysis, decision-making, and operational efficiency. By ensuring that data meets these quality attributes, organizations can leverage their data assets to achieve better outcomes and maintain trust in their data-driven processes.

At stage 310, the computing device can partition the data into training data 312 and testing data 318. The training data 312 can be used to train a regression model and the testing data 318 can be used to evaluate the model's performance. In one example, the computing device can also partition a validation data set used to tune the model and validate its performance during training. In an example, most of the data can be used as training data 312 (e.g., 70-80%) and a small portion can be reserved for testing data 318 (e.g., 10-30%).

At stage 314, the training data 312 can be used to train and optimize a regression model. As non-exhaustive examples, the regression model can be linear regression, ridge regression, lasso regression, polynomial regression, decision tree, random forest, or gradient boosting machine. Statistical learning algorithms can be implemented as needed. The statistical model selection is guided by the features present in the training data as well as the desired output of the model.

When training the model, the computing device can set up the model with initial parameters and then fit the model. For example, the computing device can use the training data 312 to train the model by finding the best-fit line (or curve) that minimizes the error between the predicted values and the actual values. For linear regression, this involves finding the line that minimizes the sum of squared residuals (the differences between observed and predicted values). For more complex models, iterative optimization techniques like gradient descent may be used to minimize the loss function.

At stage 316, the computing device can output validation data. For example, the computing device can evaluate the model using validation metrics. Some metrics for evaluating regression can include mean squared error ("MSE"), mean absolute error ("MAE"), root mean squared error ("RMSE"), and R-squared ($R^2$). The computing device can also apply cross-validation techniques to ensure the model's performance is robust and not overly dependent on the specific train-validation split. The computing device can output the results of the validation.

The computing device can also test the model using the testing data 318. For example, the computing device can apply the testing data 318 to the model and apply the same evaluation metrics. The computing device can then compare the evaluation metrics for the training data 312 and the testing data 318.

At stage 320, the computing device can finalize the regression model. For example, the computing device can continue to train, evaluate, and test the model until the results fall within an allowable tolerance of accuracy. The computing device can then store the model as a tool for predicting SARA fractions in a wellbore.

Figure 4:
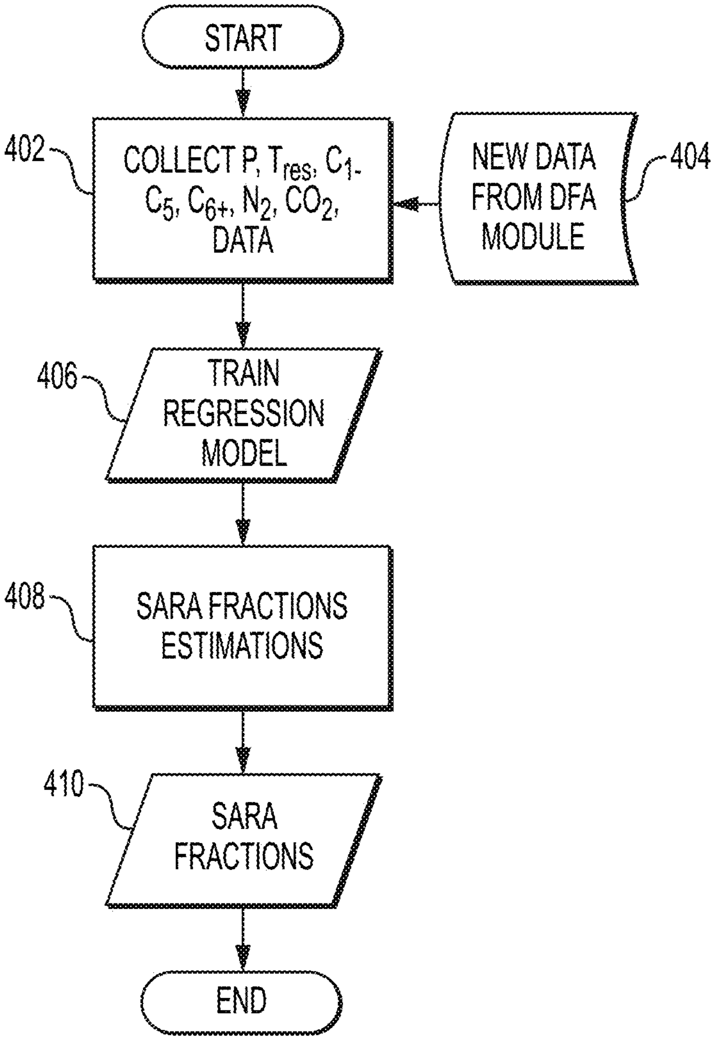
FIG. 4 is an illustration of another example workflow for estimating SARA fractions of a reservoir fluid based on data from downhole sensors.

FIG. 4 shows a workflow for using a model trained for estimating SARA fractions of a reservoir fluid based on data from downhole sensors. At stage 402, a computing device can collect data from a wellbore. This data can include P, $T_{res}$, $C_1$-$C_5$, $C_{6+}$, $N_2$, $CO_2$, SARA fractions data. At stage 404, this data can be collected from a DFA module that is part of a tool string inside the wellbore. The DFA module can provide the data using any available communication means, such as a wired or wireless connection.

At stage 406, the computing device can apply the DFA module data to a regression model. The regression model can be the regression model described previously regarding FIG. 3. In one example, the computing device can train a new regression model using the DFA module data.

At stage 408, the computing device can estimate the SARA fractions. For example, the regression model can connect distinct measurements from the DFA sensor module to different physical properties of the reservoir fluid. By inputting the DFA data into a regression model (or training a regression model using the DFA data), the regression model can show the SARA fractions data.

At stage 410, the computing device can output the SARA fractions. The SARA fractions can be output in any user-friendly way available. For example, the computing device can display a graph with the predicted versus measured SARA fraction values where the predicted values correspond to data from the DFA module and measured values correspond to data from a lab. The computing device can also present the actual values of each SARA fraction.

Other examples of the disclosure will be apparent to those skilled in the art from consideration of the specification and practice of the examples disclosed herein. Though some of the described methods have been presented as a series of steps, it should be appreciated that one or more steps can occur simultaneously, in an overlapping fashion, or in a different order. The order of steps presented are only illustrative of the possibilities and those steps can be executed or performed in any suitable fashion. Moreover, the various features of the examples described here are not mutually exclusive. Rather any feature of any example described here can be incorporated into any other suitable example. It is intended that the specification and examples be considered as exemplary only, with a true scope and spirit of the disclosure being indicated by the following claims.

What is claimed is:

1. A system, comprising:

a tool string disposed within a wellbore and comprising a downhole fluid analyzer (DFA) tool configured to collect a plurality of data samples from reservoir fluid in the wellbore, the DFA tool comprising:

a flowbore housing;

a filter array spectrometer coupled to the flowbore housing;

a fluorescence detector coupled to the flowbore housing;

a grating spectrometer coupled to the flowbore housing;

a pressure and temperature gauge coupled to the flowbore housing;

a resistivity sensor coupled to the flowbore housing; and a viscosity sensor coupled to the flowbore housing; and a processing system communicatively coupled to the DFA tool and configured to:

receive the plurality of data samples from the DFA tool;

generate a dataset of reservoir characteristics based on the plurality of data samples, wherein the dataset of reservoir characteristics comprises an indication of pressure ("P") exerted by the reservoir fluid on the flowbore housing, an indication of a temperature ("$T_{res}$") of the reservoir fluid within the flowbore housing, an indication of methane ("$C_1$") in the reservoir fluid, an indication of ethane ("$C_2$") in the reservoir fluid, an indication of propane ("$C_3$") in the reservoir fluid, an indication of butane ("$C_4$") in the reservoir fluid, an indication of pentane ("$C_5$") in the reservoir fluid, an indication of one or more hexanes ("$C_{6+}$") in the reservoir fluid, an indication of nitrogen ("$N_2$") in the reservoir fluid, and an indication of carbon dioxide ("$CO_2$") in the reservoir fluid; and determine, using a trained regression model, a predicted asphaltene stability in the reservoir fluid by generating saturates, aromatics, resins, and asphaltenes (SARA) fractions based on the dataset of reservoir characteristics.

2. The system of claim 1, wherein the filter array spectrometer of the DFA tool comprises a light source, a filter array, and a detector array.

3. The system of claim 2, wherein the detector array of the DFA tool comprises a charge-coupled device sensor or a complementary metal-oxide semiconductor sensor.

4. The system of claim 1, wherein the fluorescence detector of the DFA tool comprises an ultra-violet ("UV") light emitter and a detector, the UV light emitter emits UV light that excites particles in fluid passing through the flowbore housing, and the detector measures an intensity and a wavelength of light emitted by the excited particles.

5. The system of claim 1, wherein the grating spectrometer of the DFA tool comprises a light source, a diffraction grating, and a detector, the light source emits a light toward the diffraction grating, causing the light to diffract at specific angles based on wavelength, and the detector measures an intensity of light at each wavelength, the intensity of the light at each wavelength indicating a specific chemical in wellbore fluid.

6. The system of claim 1, wherein the pressure and temperature gauge of the DFA tool measures the pressure exerted by the reservoir fluid on the flowbore housing based on a force exerted by the reservoir fluid on a surface within the flowbore housing and measures the temperature of the reservoir fluid within the flowbore housing, and the resistivity sensor of the DFA tool measures an electrical conductivity of the reservoir fluid in the flowbore housing.

7. A method for estimating saturates, aromatics, resins, and asphaltenes ("SARA") fractions of reservoir fluid, comprising:

receiving, at a processing system, a first dataset of measurements based on a plurality of data samples of reservoir fluid retrieved from a plurality of wellbores, wherein each data sample of the plurality of data samples is associated with a wellbore of the plurality of wellbores, wherein each data sample is collected by a respective downhole fluid analyzer (DFA) tool disposed within a respective wellbore, and wherein the first dataset of measurements comprises an indication of pressure ("P") exerted by the reservoir fluid in a respective wellbore on flowbore housing of a respective DFA tool, a temperature ("$T_{res}$") of the reservoir fluid within the flowbore housing in the respective DFA tool, an indication of methane ("$C_1$") in the reservoir fluid, an indication of ethane ("$C_2$") in the reservoir fluid, an indication of propane ("$C_3$") in the reservoir fluid, an indication of butane ("$C_4$") in the reservoir fluid, an indication of pentane ("$C_5$") in the reservoir fluid, an indication of one or more hexanes ("$C_{6+}$") in the reservoir fluid, an indication of nitrogen ("$N_2$") in the reservoir fluid, and an indication of carbon dioxide ("$CO_2$") in the reservoir fluid;

training, by the processing system, a regression model to predict SARA fractions using a first subset of the first dataset of measurements;

tuning, by the processing system, the trained regression model using a second subset of the first dataset of measurements, wherein the processing system is configured to tune the regression model until a prediction performance of the regression model is greater than or equal to a prediction accuracy threshold;

instructing, by the processing system, a pump disposed within an additional wellbore to pump additional reservoir fluid from the additional wellbore into an additional DFA tool disposed within the additional wellbore;

receiving, by the processing system, a second dataset of measurements from the additional DFA tool based on the additional reservoir fluid within the additional wellbore;

providing, by the processing system, the second dataset of measurements as input to the trained regression model; and generating, by the processing system, an estimate of SARA fraction levels for the additional reservoir fluid within the additional wellbore based on the second dataset and the trained regression model.

8. The method of claim 7, wherein the trained regression model comprises at least one of a mean squared error model, a mean absolute error model, a root mean squared error model, or an R-squared model.

9. The method of claim 7, wherein the additional DFA tool comprises:

a flowbore housing;

a filter array spectrometer coupled to the flowbore housing;

a fluorescence detector coupled to the flowbore housing;

a grating spectrometer coupled to the flowbore housing;

a pressure and temperature gauge coupled to the flowbore housing;

a resistivity sensor coupled to the flowbore housing; and a viscosity sensor coupled to the flowbore housing.

10. The method of claim 9, wherein the filter array spectrometer, the fluorescence detector, and the grating spectrometer of the additional DFA tool collectively record wavelength and intensity measurements, and wherein the method further comprises identifying particles in the additional reservoir fluid within the additional wellbore based on the wavelength and intensity measurements.

11. The method of claim 9, wherein the pressure and temperature gauge of the additional DFA tool:

generates a measurement of pressure in the additional wellbore based on measuring a force exerted by the additional reservoir fluid on a surface within the flowbore housing; and generates a measurement of temperature in the additional wellbore based on measuring a temperature of the additional reservoir fluid within the flowbore housing of the additional DFA tool.

12. The method of claim 11, wherein the resistivity sensor of the additional DFA tool measures an electrical conductivity of the additional reservoir fluid in the flowbore housing.

13. A system for estimating saturates, aromatics, resins, and asphaltenes ("SARA") fractions in reservoir fluid, comprising:

a downhole fluid analyzer (DFA) tool configured to receive a sample of reservoir fluid from a wellbore and collect a plurality of data samples associated with the reservoir fluid, the DFA tool, comprising:

a flowbore housing;

an isolation valve coupled to the flowbore housing;

a filter array spectrometer coupled to the flowbore housing;

a fluorescence detector coupled to the flowbore housing;

a grating spectrometer coupled to the flowbore housing;

a pressure and temperature gauge coupled to the flowbore housing;

a resistivity sensor coupled to the flowbore housing; and a viscosity sensor coupled to the flowbore housing;

a pump disposed within the wellbore and coupled to the isolation valve of the DFA tool via tubing, wherein the pump is configured to pump the reservoir fluid from the wellbore into the DFA tool; and a computing system configured to perform operations comprising:

causing the pump to pump the reservoir fluid to the isolation valve of the DFA tool;

causing the DFA tool to collect the plurality of the data samples;

receiving the plurality of data samples from the DFA tool;

generating a dataset of reservoir characteristics based on the plurality of data samples, wherein the dataset of reservoir characteristics comprises an indication of pressure ("P") exerted by the reservoir fluid on the flowbore housing, a temperature ("$T_{res}$") of the reservoir fluid within the flowbore housing, an indication of methane ("$C_1$") in the reservoir fluid, an indication of ethane ("$C_2$") in the reservoir fluid, an indication of propane ("$C_3$") in the reservoir fluid, an indication of butane ("$C_4$") in the reservoir fluid, an indication of pentane ("$C_5$") in the reservoir fluid, an indication of one or more hexanes ("$C_{6+}$") in the reservoir fluid, an indication of nitrogen ("$N_2$") in the reservoir fluid, and an indication of carbon dioxide ("$CO_2$") in the reservoir fluid; and determining, using a trained regression model, a predicted asphaltene stability in the reservoir fluid by generating a prediction of the SARA fractions in the reservoir fluid based on the dataset of reservoir characteristics.

14. The system of claim 13, wherein the filter array spectrometer of the DFA tool comprises a light source, a filter array, and a detector array.

15. The system of claim 14, wherein the detector array of the DFA tool comprises a charge-coupled device sensor or a complementary metal-oxide semiconductor sensor.

16. The system of claim 13, wherein the fluorescence detector of the DFA tool comprises an ultra-violet ("UV") light emitter and a detector, the UV light emitter emits UV light that excites particles in fluid passing through the flowbore housing, and the detector measures an intensity and a wavelength of light emitted by the excited particles.

17. The system of claim 13, wherein the grating spectrometer of the DFA tool comprises a light source, a diffraction grating, and a detector, the light source emits a light toward the diffraction grating, causing the light to diffract at specific angles based on wavelength, and the detector measures an intensity of light at each wavelength, the intensity of the light at each wavelength indicating a specific chemical in the reservoir fluid.

18. The system of claim 13, wherein the pressure and temperature gauge of the DFA tool measures the pressure exerted by the reservoir fluid on the flowbore housing based on a force exerted by the reservoir fluid on a surface within the flowbore housing and measures the temperature of the reservoir fluid within the flowbore housing.

19. The system of claim 1, wherein the SARA fractions correspond to respective solubilities of the saturates, the aromatics, the resins, and the asphaltenes within the reservoir fluid in a plurality of solvents, wherein the saturates, the aromatics, the resins, and the asphaltenes each correspond to a range of molecular-weight species.

20. The method of claim 7, wherein the regression model is trained to predict the SARA fractions based on additional data samples comprising SARA measurements for each of the plurality of wellbores.

* * * * *